United States Patent
Ohmi

[11] Patent Number: 5,438,001
[45] Date of Patent: Aug. 1, 1995

[54] METHOD AND DEVICE FOR MEASURING VARIATION IN DECOMPOSITION RATE OF SPECIAL MATERIAL GAS

[76] Inventor: Tadahiro Ohmi, 1-17-301, Ko-megabukuro 2-chome, Aoba-ku Miyagi-ken Sendai-shi, Japan

[21] Appl. No.: 150,128
[22] PCT Filed: May 13, 1992
[86] PCT No.: PCT/JP92/00606
 § 371 Date: Jan. 31, 1994
 § 102(e) Date: Jan. 31, 1994
[87] PCT Pub. No.: WO92/21967
 PCT Pub. Date: Oct. 12, 1992

[30] Foreign Application Priority Data

May 31, 1991 [JP] Japan .................................. 3-157653

[51] Int. Cl.$^6$ ............................................. G01N 30/06
[52] U.S. Cl. ............................................ 436/34; 436/72; 204/192.13; 204/192.33; 422/89
[58] Field of Search ............... 436/34, 72; 204/192.33, 204/192.1, 192.13, 192.30; 252/964; 73/855; 422/89

[56] References Cited

U.S. PATENT DOCUMENTS 3,578,404 5/1971 Walles et al. ......................... 436/34
4,810,654 3/1989 Tao ...................................... 436/72

Primary Examiner—Robert J. Warden
Assistant Examiner—N. Bhat
Attorney, Agent, or Firm—Young & Thompson

[57] ABSTRACT

A method and a device for measuring detailed decomposition rate characteristic of special material gas such as silane gas. After inert gas is supplied from a gas purifier(1)(a first gas-supply source) into a reaction pipe(20) to provide a high purity atmosphere in the pipe, the inside of the pipe is baked by heater (25 or 27). Then, the inside of the reaction pipe(20) is kept in an atmosphere at a specified temperature and special material gas with a specified purity is supplied from a bomb(10)(a second gas-supply source) into the reaction pipe at a fixed flow rate. When the inside of the reaction pipe (20) reaches a specified terminal temperature, a decomposition rate of the special material gas at the temperature is measured by a gas chromatography (12) by, for example, extracting a part of gas in the reaction pipe. Afterward, a flow rate of the special material gas is successively varied and a decomposition rate at every time of variation is measured. Further, an atmosphere inside the reaction pipe (20) is successively set to one at another specified temperature for measuring a decomposition rate at every temperature. With an impurity concentration in the special gas varied, the measuring is repeated.

5 Claims, 2 Drawing Sheets

METHOD AND DEVICE FOR MEASURING VARIATION IN DECOMPOSITION RATE OF SPECIAL MATERIAL GAS

FIELD OF THE INVENTION

The present invention relates to a method and device for accurately measuring the decomposition rate of various special material gases which are necessary for semiconductor manufacturing, in relation to reaction time, impurity concentration, atmospheric temperature, and the like.

BACKGROUND OF THE INVENTION

In recent semiconductor manufacturing technology, for example, in the case in which a silicon substrate is manufactured, the handling of special material gases (for example, silane gas, disilane gas, diborane gas, and the like) is extremely important, and an elucidation of the chemical and physical properties thereof would lead to great developments in such manufacturing technology. Such special material gases are corrosive, spontaneously combustive, and toxic; such properties make the handling thereof inconvenient, and they decompose as the result of specified temperatures or discharges; for example, in the case in which this special material gas comprises silane gas (SiH$_4$), it is known that this gas decomposes into Si and 2H$_2$, and the decomposition temperatures thereof have been measured.

Conventionally, the component analyses of such special material gases were carried out using concentration analyzers utilizing gas chromatography.

However, conventionally, only approximate values were known for the decomposition temperatures of special material gases, and no useful data could be obtained with respect to the relationship between various reaction conditions and variations in the decomposition rate. Accordingly, in particular with respect to manufacture of semiconductors having hyperfine structures, sufficient understanding of these relationships is necessary.

The present invention was created in light of the above-described problems in the background art; it has as an object thereof to provide a method and device for easily and accurately measuring the relationship between the decomposition rate of special material gasses which present difficulties in handling, and reaction conditions such as reaction time, impurity concentration, and atmospheric temperature.

SUMMARY OF THE INVENTION

In order to achieve the above object, the invention relates to a method for measuring variation in a decomposition rate of a special material gas, which comprises a first step, in which an inert gas of ultrahigh purity is caused to flow in a reaction pipe, an inner surface of which has been subjected to electrolytic polishing so as to be stable with respect to at least special material gases; a second step, in which the interior of this reaction pipe is baked so as to achieve a specified purity level; a third step, wherein the interior of the reaction pipe is placed in an atmosphere having a specified temperature; a fourth step, in which a special material gas having a specified purity is supplied at a specified flow rate into the reaction pipe; and a fifth step, in which the decomposition rate of the special material gas within the reaction pipe is measured under varying flow rate, purity, and reaction pipe atmospheric temperature conditions; silane gas is used as a representative special material gas.

The invention also relates to a device for measuring variation in a decomposition rate of a special material gas, which comprises a first gas supply source for supplying an inert gas of high purity, a second gas supply source for supplying a special material gas at adjustable concentrations and flow rates, a purity adjustment mechanism which is capable of adjusting an amount of impurities added to this special material gas, changeover valves which are capable of selective changeover between an inert gas and a special material gas flow, a support mechanism for supporting a reaction vessel, one end opening of which is connected to a valve, a concentration analyzer, which is connected to the other end opening of the reaction pipe, and a heating mechanism which is capable of controlling the interior of the reaction pipe so as to maintain a freely selected fixed temperature; gas chromatography is used as a representative of the concentration analyzer.

First, by causing an argon gas of high purity to flow into a reaction pipe, an interior surface of which has been subjected to electrolytic polishing, the interior of the reaction pipe is placed in an atmosphere having a high purity level. Next, the heating mechanism is engaged, and the interior of the reaction pipe is subjected to baking. In so doing, the interior of the reaction pipe is placed in an atmosphere of ultrahigh purity of at least a background level. Next, the heating mechanism is controlled so as to place the interior of the reaction pipe in an atmosphere having a specified temperature. After this, a special material gas (for example, silane gas) having a specified impurity concentration is caused to flow into the reaction pipe at a specified flow rate.

In this state, the impurity concentration of the special material gas and the atmospheric temperature within the reaction pipe are each maintained at specified fixed values, and next, the flow rate of the special material gas is successively varied, and the decomposition rate of the special material gas at each flow rate is measured.

Next, one or both of the impurity concentration of the special material gas and the atmospheric temperature within the reaction pipe are maintained at differing specified values, the flow rate is successively varied in the above manner, and the decomposition rate is measured with respect to various impurity concentrations and atmospheric temperatures.

The reaction pipe is stable with respect to special material gases, so that no corrosion is caused by supplying a special material gas, and there is no effect on the measurement results of the special material gas itself.

(Description of the References)

Figure 1:
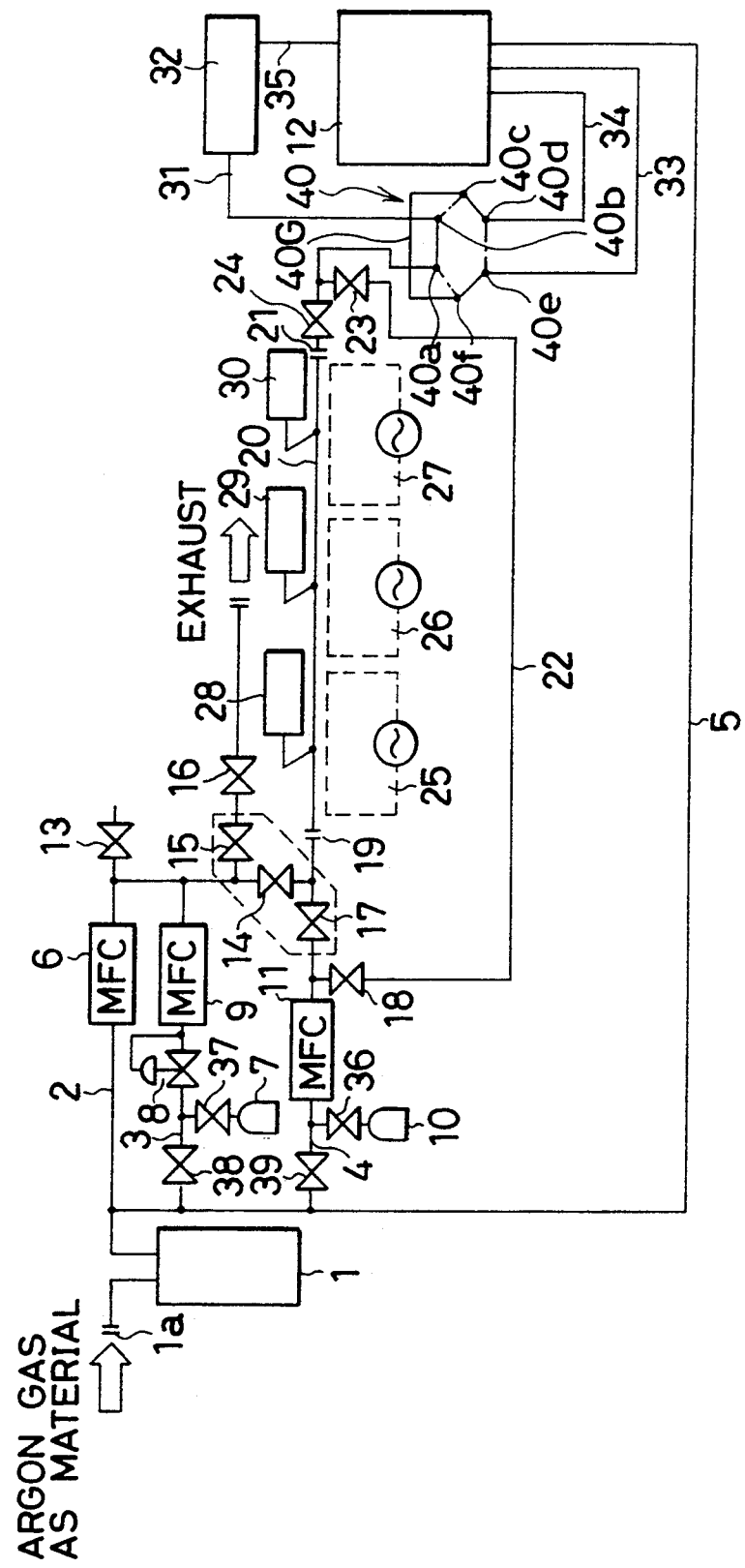
FIG. 1 is a gas flow diagram showing an example of a device which is used to execute the method for measuring variation in a decomposition rate in accordance with the present invention.

1 gas purifier (first gas supply source)
6 first gas flow control meter
8 regulator (purity adjustment mechanism)
9 second gas flow control meter
10 bomb (second gas supply source)

third gas flow control meter
12 gas chromatograph (concentration analyzer)
17, 21 gas joint (support mechanism)
20 reaction pipe
25, 26, 27 heaters (heating mechanisms)

DETAILED DESCRIPTION OF THE INVENTION

FIG. I shows an example of a device for executing the method for measuring variation in the decomposition rate of a special material gas in accordance with the present invention. As shown in the diagram, a supply source (not depicted in the diagram) for an inert source gas such as argon gas is connected to the gas input side of purifier 1 through the medium of gas joint 1a, and first through fourth gas supply lines 2–5 are connected to the gas output side thereof.

A first gas flow control meter (MFC) 6 is connected to the first gas supply line 2, a first bomb 7, which serves as an impurity supply source (moisture supply source), a regulator 8, and a second MFC 9 are connected to the second gas supply line 3, in that order, from the upstream side thereof, and a second bomb 10, which serves as a special material gas (silane gas) supply source, and a third MFC 11 are connected to the third gas supply line 4, in that order, from the upstream side thereof. Furthermore, a gas chromatograph (GC) 12 is connected to the downstream end side of the fourth gas supply line 5 as a concentration analyzer.

A first valve 13 is connected to the downstream side of the first MFC 6, and second and third valves 14 and 15 are connected at the conflux portion on the downstream side of both the first and second MFCs 6 and 9, and third valve 15 is connected to an exhaust mechanism through the medium of fourth valve 16.

Furthermore, a fifth valve 17 and a sixth valve 18 are connected to the downstream side of the third MFC 11, and a first joint 19 is connected at the downstream side of the conflux portion of second valve 14 and fifth valve 17 as a support mechanism. First joint 19 is connected to the upstream side end of reaction pipe 20, and a second joint 21 is connected to the downstream side end of reaction pipe 20 as a support mechanism.

Furthermore, sixth valve 18 is connected to the upstream side end of bypass line 22, and the downstream side end of bypass line 22 is connected to the downstream side of eighth valve 24 through the medium of seventh valve 23, while the upstream side of eighth valve 24 is connected to the second joint 21.

Heaters 25, 26, and 27, which serve as heating mechanisms, are provided along the longitudinal direction of reaction pipe 20, and furthermore, temperature detectors 28, 29, and 30 are provided for each heating region of each heater.

The downstream conflux point of seventh and eighth valves 23 and 24 is connected to the first junction point 40a of sampling device 40. Sampling device 40 comprises this first junction point 40a as well as second through sixth junction points (40b, 40c, 40d, 40c, and 40f) arranged in a ring form; first junction point 40a is selectively coupled to second junction point 40b and sixth junction point 40e, while third junction point 40c is selectively coupled with second junction point 40b and fourth junction point 40d, and fifth junction point 40e is selectively coupled with fourth junction point 40d and sixth junction point 40f. Furthermore, sampling pipe 40G is connected between third junction point 40c and sixth junction point 40f.

Furthermore, an exhaust gas processing device 32 is connected to second junction point 40b through the medium of a gas exhaust line 31, and fourth junction point 40d and fifth junction point 40e are connected to GC 12 through the medium of gas inlet line 33 and gas outlet line 34, respectively. Fourth gas supply line 5 is connected to gas inlet line 33 in GC 12, and gas outlet line 34 is connected to exhaust gas processing device 32 through the medium of gas blow-off line 35.

On second gas supply line 3, a ninth valve 38 is connected on the upstream side of regulator 8, and a tenth valve 37 is connected between the downstream side of this ninth valve 38 and bomb 7. Furthermore, an eleventh valve 39 is connected to the upstream side of MFC 11 on third gas supply line 4, while a twelfth valve 36 is connected between the downstream side of eleventh valve 39 and bomb 10.

Each valve 13, 14, 15, 16 . . . is completely constructed of metal, and the discharge gases from the interior of each of these valves Is regulated so as not to worsen the purity of the gas passing therethrough.

Next, a measurement method in accordance with the present invention and utilizing the above construction will be described.

First, a stainless steel pipe having dimensions such that the pipe diameter thereof is ¼ inches and the length thereof is 2 meters, an inner surface of which is subjected to electrolytic polishing, and which is subjected to processing so as to be stable with respect to special material gasses (in the case of the present example, silane gas) is prepared for use as reaction pipe 20, and this is placed between couplings 19 and 21.

Next, the first, second, sixth, seventh, tenth, and twelfth valves 13, 14, 18, 23, 37, and 36 are closed, and the other valves, that is to say, the third, fourth, fifth, eighth, ninth, and eleventh valves 15, 16, 17, 18, 23, 24, 38, and 39 are opened. In so doing, the first and second gas supply lines 2 and 3, and the third and fourth gas supply lines 4 and 5 are purged by means of argon gas of ultrahigh purity, and the reaction pipe 20 is also purged. At this time, sampling device 40 is, as shown by the dotted lines in FIG. 1, such that first junction point 40a is connected with sixth junction point 40f, second junction point 40b is connected with third junction point 40c, and fifth junction point 40e is connected with fourth junction point 40d. Accordingly, the gas blow-off line 31, as well as the gas inlet line 33 and the gas outlet line 34, are also purged by means of argon gas.

In this state, heaters 25, 26, and 27 are engaged, and the interior of reaction vessel 20 is baked, so that the impurities adhering to the inner wall of reaction pipe 20 are caused to desorb. When this baking has been completed, heaters 25, 26, and 27 within reaction pipe 20 are controlled based on the output of temperature detectors 28, 29, and 30 in order to set the interior of reaction pipe 20 to a specified temperature (for example, 23° C.).

Next, after the second valve 14 has been opened, and the third, fourth, fifth, eighth, ninth, and eleventh valves 15, 16, 17, 24, 38, and 39 have been closed, the twelfth valve 36 is opened, and furthermore, the sixth valve 18 and the seventh valve 23 are also opened. Argon gas is flowing within reaction pipe 20; however, as a result of this, silane gas flows into bypass line 22, and silane gas can be caused to flow into reaction pipe 20.

After this, sixth and seventh valves 18 and 23 are closed, and fifth and eighth valves 17 and 24 are opened. As a result of this, a mixture of argon gas and silane gas is caused to flow into reaction pipe 20 at a specified flow rate; however, the mixture ratio of both gases is set so that, for example, 15% of silane gas is contained in the argon gas. It is possible to adjust this mixture ratio as desired by means of the control amounts of first MFC 6 and third MFC 11.

When this mixed gas is caused to flow into reaction pipe 20 at a specified flow rate, and the decomposition reaction of the silane gas has proceeded for a specified period of time, sampling device 40 is operated, and as shown by the solid lines in FIG. 1, the first junction point 40a is connected to the second junction point 40b, the third junction point 40c is connected to the fourth junction point 40d, and the fifth junction point 40e is connected to the sixth junction point 40f. As a result of this, the mixed gas contained in sampling pipe 40G is introduced into GC 12 through the medium of gas outlet line 34, and the amount of silane gas contained at this flow rate, that is to say, the decomposition rate of the silane gas, is measured.

When the measurement at this specified flow rate has been completed, the setting of the sampling device 40 is altered so that the connection state of each junction point returns to that shown by the dotted lines in FIG. 1, first MFC 6 and third MFC 11 are adjusted so as to successively set other specified flow rates, and measurement identical to that described above is repeated for each flow rate.

Next, heaters 25, 26, and 27 are controlled so as to successively set the interior of reaction pipe 20 to other specified temperatures, and the measurement of the decomposition rate by means of GC 12 is repeated in a manner identical to that described above for each temperature.

When the impurity amount, that is to say, the moisture amount, contained in the mixed gas is varied, and measurement is conducted, the tenth valve 37 is opened, and the regulator is set. It is also possible to measure this moisture concentration in the mixed gas by means of GC 12.

Figure 2:
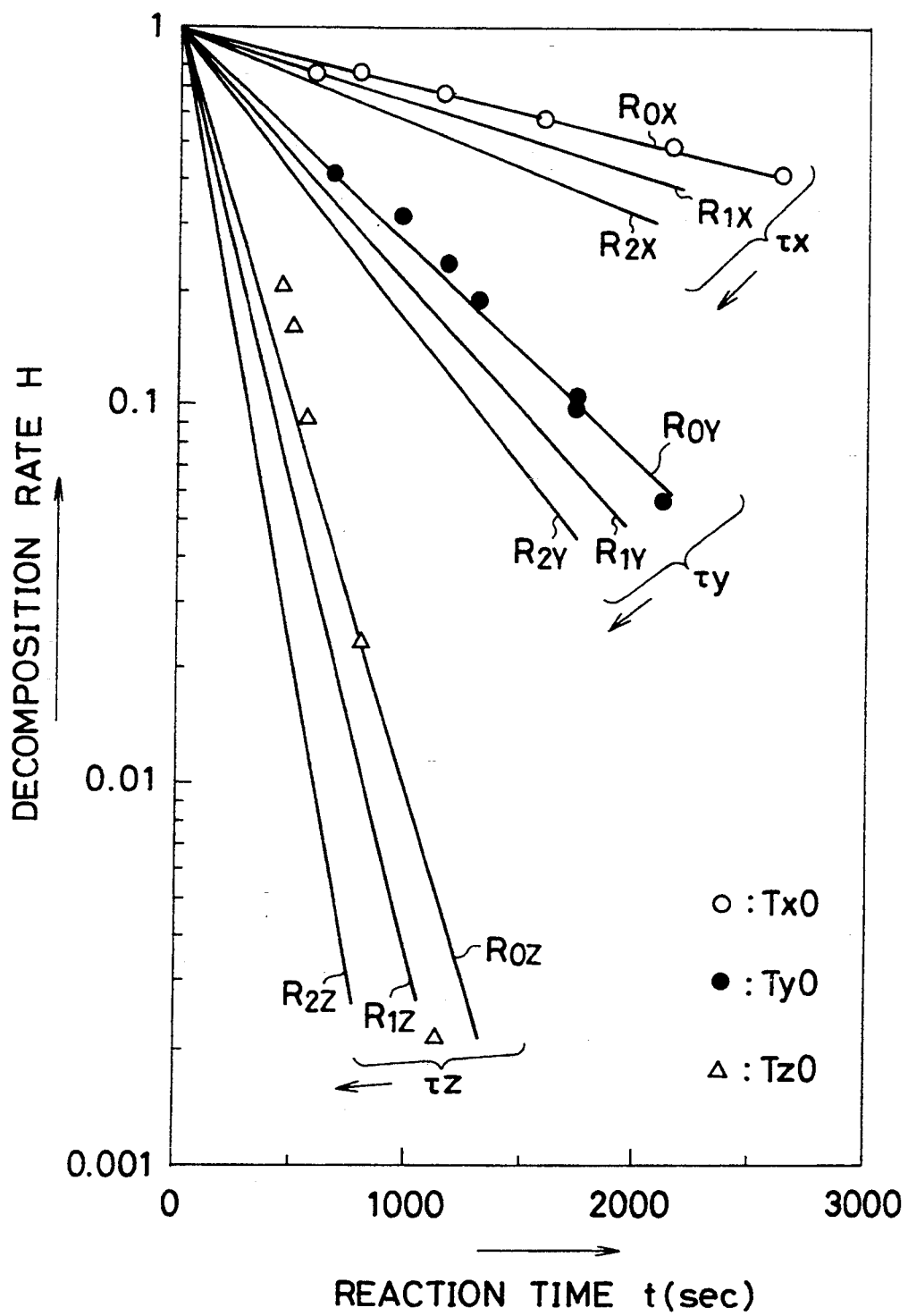
FIG. 2 is a graph showing an example of measurements obtained by means of the device depleted in FIG. 1.

FIG. 2 shows the result of the data obtained by means of the above measurements; the horizontal axis indicates the reaction time t, while the vertical axis indicated the decomposistion rate H. The plots indicated by white circles, black circles, and triangles in the diagram indicate cases in which the atmospheric temperature T within reaction pipe 20 was, respectively $T_{XO}$ (380° C.), $T_{YO}$ (400° C.), and $T_{XO}$ (415° C.); straight lines $R_{0X}$, $R_{0Y}$, and $R_{0X}$ while the straight lines $R_{1X}$, $R_{1Y}$, and $R_{1Z}$ as well as straight lines $R_{2X}$, $R_{2Y}$, and $R_{2Z}$ correspond to cases in which the moisture concentration R was $R_1$ and $R_1$, respectively. Here, the moisture concentration R increases in the order $R_0$, $R_1$, and $R_2$.

Furthermore, the group of straight lines $R_{0X}$, $R_{1X}$, and $R_{2X}$ correspond to cases in which the lifetime $\tau$ (expressed by the inverse of the speed constant k of the decomposition reaction) of silane gas is $\tau_X$ (2835 secs), while the group of straight lines $R_{0Y}$, $R_{1Y}$, $R_{2Y}$, and the group of straight lines $R_{0X}$, $R_{1Z}$, $R_{2Z}$, correspond to cases in which the lifetime $\tau$ was, respectively, $\tau_Y$ (755 secs), and $\tau_Z$ (208 secs).

Accordingly, as can be understood from the diagram, the decomposition of the silane gas proceeded in the order $R_0$, $R_1$, $R_2$, of the moisture content R contained therein; that is to say, this decomposition proceeded more quickly as the moisture concentration R increased.

From the characteristics exhibited by the straight lines $R_{0X}$, $R_{0Y}$, $R_{0Z}$ . . . shown in the diagram, it is thought that the relationship between the decomposition rate H of the silane gas and the reaction time t is expressed by the formula given below. This relationship should be considered in terms of separate cases in which moisture is not contained (formulas 1–6) and cases in which moisture is contained (formulas 7–11).

First, it is possible to express the variance rate over time of a concentration N of silane gas in the case in which moisture is not contained by means of the formula 1 given below.

$$-dN/d\tau = (1/\tau)N \qquad \text{Formula 1}$$

When the separation of the variables of Formula 1 is conducted and integration is performed within a specified integral domain having both boundaries, the following Formula 2 results.

$$-\int_{N_o}^{N_t}(1/N)dN = \int_o^t kdt \qquad \text{Formula 2}$$

in the above Formula 2, $N_o$ indicates the initial concentration of silane gas, while $N_t$ indicates the concentration after a period of time t.

The Formula 3 shown below represents the result of the integration of Formula 2.

$$l_n(N_t/N_o) = -kt \qquad \text{Formula 3}$$

Here, if X represents the decomposed silane concentration, then $N_t$ is expressed by means of Formula 4 below.

$$N_t = N_o - X \qquad \text{Formula 4}$$

Accordingly, the decomposition rate H of the silane gas is given by Formula 5 below.

$$H = (N_o - X)/N_o = exp(-k/\tau) \qquad \text{Formula 5}$$

Accordingly, the remaining concentration Q of the silane gas is given by Formula 6 below.

$$Q = N_o - X = N_o \exp(-t/\tau) \qquad \text{Formula 6}$$

Next, in the case in which moisture is contained in the silane gas, if M represents the moisture concentration in the silane gas, then the variance rate over time of concentration N is given by the Formula 7 below. In Formula 7, $k_1$ and $k_2$ indicate speed constants; the former indicates a constant in which moisture is not taken into account, while the latter is a constant in which moisture is taken into account.

$$-dN/dt = k_1 \cdot N + k_1 \cdot M \cdot N \qquad \text{Formula 7}$$

If variable separation of Formula 7 is conducted and integration is conducted over a specified integral domain, the Formula 8 shown below is obtained.

$$(N-X)/N_o = exp(-k_1 \cdot t - k_2 \cdot M \cdot t) \qquad \text{Formula 8}$$

Accordingly, the remaining concentration Q of the silane gas concentration is given by Formula 9 below.

$$Q = N_o - X = exp(-_1 \cdot t - k_2 M \cdot t) \qquad \text{Formula 9}$$

Based on Formula 9, the effective speed constant $k_{eff}$ in the case in which the presence of moisture is included, and the effective lifetime $\tau_{eff}$, are defined as shown in Formula 10 below.

$$k_{eff}=k_1+k_2 \cdot M = 1/t_{eff}=(1/t_1)=(M/\tau_2) \qquad \text{Formula 10}$$

From the above formulas, it can be understood that as the amount of moisture contained in the special material gas increases, the speed of decomposition also increases.

Industrial Applicability

In accordance with the invention the method comprises a first step, in which an inert gas of ultrahigh purity is caused to flow in a reaction pipe, an inner surface of which has been subjected to electrolytic polishing so as to be stable with respect to at least special material gasses; a second step, in which the interior of this reaction pipe is baked so as to achieve a specified purity level; a third step, wherein the interior of the reaction pipe is placed in an atmosphere having a specified temperature; a fourth step, in which a special material gas having a specified purity is supplied at a specified flow rate into the reaction pipe; and a fifth step, in which the decomposition rate of the special material gas within the reaction pipe is measured under varying flow rate, purity, and reaction pipe atmospheric temperature conditions; so that it is possible to accurately analyze all characteristics pertaining to variation in decomposition rates with respect to special material gases such as silane gas, and the like, which are important in semiconductor manufacture, and this contributes in particular to the manufacture of semiconductors possessing hyperfine structures.

In accordance with the invention the device comprises a first gas supply source for supplying an inert gas of high purity, a second gas supply source for supplying a special material gas at adjustable concentrations and flow rates, a purity adjustment mechanism which is capable of adjusting an amount of impurities added to this special material gas, change-over valves which are capable of selective changeover between an inert gas and a special material gas flow, a support mechanism for supporting a reaction pipe, one end opening of which is connected to a valve, a concentration analyzer, which is connected to the other end opening of the reaction pipe, and a heating mechanism which is capable of controlling the interior of the reaction pipe so as to maintain a freely selected fixed temperature; so that, by utilizing a gas supply system or gas analyzer which is easily employable by humans, it is possible to easily execute the invention as recited.

What is claimed is:

1. A method for measuring variation in a decomposition rate of a material gas which decomposes during manufacture of semiconductors, which comprises: a first step, in which an inert gas of ultrahigh purity is caused to flow in a reaction pipe, an inner surface of which has been subjected to electrolytic polishing so as to be stable with respect to at least said material gas; a second step, in which an interior of said reaction pipe is baked so as to achieve a specified purity level; a third step, wherein said interior of said reaction pipe is placed in an atmosphere having a specified temperature; a fourth step, in which a material gas having a specified purity is supplied at a specified flow rate into said reaction pipe; and a fifth step, in which a decomposition rate of said material gas within said reaction pipe is measured under varying flow rate, purity, and reaction pipe atmospheric temperature conditions.

2. A method for measuring variation in a decomposition rate of a material gas in accordance with claim 1, wherein said material gas comprises silane gas.

3. A method for measuring variation in a decomposition rate of a material gas in accordance with claim 1, wherein said material gas is selected from the group consisting of silane, disilane and diborane.

4. A device for measuring variation in a decomposition rate of a material gas which decomposes during manufacture of semiconductors, which comprises: a first gas supply source for supplying an inert gas of high purity, a second gas supply source for supplying a material gas at adjustable concentrations and flow rates, a purity adjustment mechanism including means for adjusting an amount of impurities added to said material gas, changeover valve means for selectively changing over between an inert gas and a special material gas flow, a support mechanism for supporting a reaction pipe, one end opening of said reaction pipe being connected to a valve, a concentration analyzer, connected to another end opening of said reaction pipe, and a heating mechanism for controlling an interior of said reaction pipe so as to maintain a freely selected fixed temperature.

5. A device for measuring variation in a decomposition rate of a material gas in accordance with claim 4, wherein said concentration analyzer comprises a gas chromatograph.

* * * * *